United States Patent [19]

Sappey

[11] Patent Number: 5,738,101
[45] Date of Patent: Apr. 14, 1998

[54] OPTICAL IMAGING THROUGH TURBID MEDIA WITH A DEGENERATE FOUR-WAVE MIXING CORRELATION TIME GATE

[75] Inventor: Andrew D. Sappey, Golden, Colo.

[73] Assignee: The Regents of the University of California, Los Alamos, N. Mex.

[21] Appl. No.: 588,171

[22] Filed: Jan. 18, 1996

[51] Int. Cl.$^6$ ...................................................... A61B 6/00
[52] U.S. Cl. ........................................... 128/665; 356/345
[58] Field of Search ....................... 128/664–665, 128/633; 356/345; 250/341.1, 358.1

[56] References Cited

U.S. PATENT DOCUMENTS 5,371,368  12/1994  Alfano et al. ............................ 128/664
5,530,544  6/1996   Trebino et al. .......................... 356/345

OTHER PUBLICATIONS

Andrew D. Sappey, "Optical Imaging Through Turbid Media with a Degenerate Four Wave Mixing Correlation Time Gate," Appl. Opt. 33, 8346 (1994).

K.M. Yoo et al., "Imaging Of A Translucent Object Hidden In A Highly Scattering Medium From The Early Portion Of The Diffuse Component Of A Transmitted Ultrafast Laser Pulse," Opt. Lett. 17, 958 (1992).

K.M. Yoo et al., "Imaging Objects Hidden In Highly Scattering Media Using Femtosecond–Harmonic–Generation Cross–Correlation Time Gating," Opt. Lett. 16, 1019 (1991).

J. Reintjes et al. "Time–Gated Imaging With Nonlinear Optical Raman Interactions," Opt. & Photonics News, p. 28–32 (1993).

M. D. Duncan et al., in "Time–Gated Imaging Through Scattering Media Using Stimulated Raman Amplification," Opt. Lett. 16, 1868 (1991).

H. Chen et al., "Two–Dimensional Imaging Through Diffusing Media Using 150–fs Gated Electronic Holography Techniques," Opt. Lett. 16, 487 (1991).

R. Vijaya et al., "Optical Phase Conjugation In Laser Dyes," Opt. Quant. Electron. 24, 575 (1992).

D. M. Bloom et al., "Observation Of Amplified Reflection By Degenerate Four–Wave Mixing In Atomic Sodium Vapor," Opt. Lett. 2, 58 (1978).

*Primary Examiner*—Ruth S. Smith
*Attorney, Agent, or Firm*—Samuel M. Freund

[57] ABSTRACT

Optical imaging through turbid media is demonstrated using a degenerate four-wave mixing correlation time gate. An apparatus and method for detecting ballistic and/or snake light while rejecting unwanted diffusive light for imaging structures within highly scattering media are described. Degenerate four-wave mixing (DFWM) of a doubled YAG laser in rhodamine 590 is used to provide an ultrafast correlation time gate to discriminate against light that has undergone multiple scattering and therefore has lost memory of the structures within the scattering medium. Images have been obtained of a test cross-hair pattern through highly turbid suspensions of whole milk in water that are opaque to the naked eye, which demonstrates the utility of DFWM for imaging through turbid media. Use of DFWM as an ultrafast time gate for the detection of ballistic and/or snake light in optical mammography is discussed.

12 Claims, 6 Drawing Sheets

OPTICAL IMAGING THROUGH TURBID MEDIA WITH A DEGENERATE FOUR-WAVE MIXING CORRELATION TIME GATE

FIELD OF THE INVENTION

The present invention relates generally to optical imaging and, more particularly, to imaging structures inside highly scattering media using degenerate four-wave mixing (DFWM) of laser light to discriminate against light that has undergone multiple scattering and has thereby lost memory of the structures therein. The invention was made with government support under Contract No. W-7405-ENG-36 awarded by the U.S. Department of Energy to The Regents of The University of California. The government has certain rights in the invention.

BACKGROUND OF THE INVENTION

Significant effort has been expended to advance the field of optical mammography. In spite of improvements, the technology has not been able to offer a practical alternative to current x-ray systems. However, the promise of optical technology offers definite advantages over existing technology in that nonionizing radiation would be used to locate tumors in the earliest stages of development.

When a collimated pulse of photons transits a highly turbid medium, the transmitted light contains three temporal components: ballistic, snake, and diffusive. The diffusive component is composed of multiply scattered photons that are the last to exit the sample because they traveled the longest distance to their exit point. This component is the most intense for highly scattering media, but all memory of internal structure is lost because of the multiple-scattering events. Ballistic photons take the shortest path through the object, retain the most information regarding structures inside the medium, and exit first. However, such photons are extremely rare or nonexistent in highly turbid media. The snake component arises from photons that are scattered within a small forward-directed angular cone. These photons arrive at the onset of the diffusive component, but retain significant information about the hidden structures.

To obtain images of structures within the scattering medium, ballistic and/or snake photons must be detected, while the more numerous diffusive photons are rejected. A number of techniques preferentially detect the early light based on its spatial, coherence, or temporal properties. As an example, Fourier filtering of the ballistic light is possible when a well-collimated source illuminates the sample because these photons do not deviate significantly from parallel ray trajectories. Therefore, a lens of focal length f placed a distance f from the scattering medium focuses a distance 2f from the scattering medium, whereas the photons that comprise the diffusive component have nearly random trajectories, forming thereby an extended source for the lens. Such rays are collimated by the lens so that an iris placed at the focal plane of the lens transmits the early light and rejects most of the diffusive light.

Time gating with coherent or electronic techniques can also be used to reject he diffusive light. Ultrafast electronic gating of an imaging device has been used to accurately locate a nearly translucent piece of chicken fat 2.5 mm thick that was embedded in a 4 cm thick piece of chicken breast tissue. A 20 ps time-gated streak camera was used to record the early light exiting the sample. See, e.g., "Imaging Of A Translucent Object Hidden In A Highly Scattering Medium From The Early Portion Of The Diffuse Component Of A Transmitted Ultrafast Laser Pulse," by K. M. Yoo et al., Opt. Lett. 17, 958 (1992). Yoo et al. have also imaged objects hidden in highly scattering media suing femtosecond second-harmonic-generation time gating. See, e.g., "Imaging Objects Hidden In Highly Scattering Media Using Femtosecond Second-Harmonic-Generation Cross-Correlation Time Gating," by K. M. Yoo et al., Opt. Lett. 16, 1019 (1991). Therein the authors describe the use of second-harmonic generation in nonlinear crystals to discriminate against diffusive light. Ultrafast pulses from a femtosecond laser are split into a sample and a reference beam. After passing through the turbid medium, the sample beam is recombined spatially and temporally with the reference beam in a nonlinear crystal. Light at the second-harmonic frequency contains a shadowgram of structures inside the scattering medium.

J. Reintjes et al. have used stimulated Raman scattering (SRS) to create a fast time gate. See, e.g., "Time-Gated Imaging With Nonlinear Optical Raman Interactions," Opt. & Photonics News, pages 28–32 (1993), and "Time-Gated Imaging Through Scattering Media Using Stimulated Raman Amplification," by M. D. Duncan et al., Opt. Lett. 16, 1868 (1991). SRS can be implemented as a pulsed gating technique that requires an ultrafast-pulsed laser or as a correlation gating technique that can be used with long-pulse or cw lasers. SRS is a nonlinear Raman interaction that occurs in suitable materials such as hydrogen gas. In SRS, a long-wavelength (Stokes) beam is amplified by a shorter wavelength pump beam. The difference in wavelength between the Stokes and the pump beams is constrained to be equal to a fundamental vibrational frequency of the medium in which the interaction occurs (hydrogen). Reintjes et al. use a mode-locked doubled Nd:YAG laser (532 nm) to provide picosecond pulses. The output is split into sample and reference beams, and an optical delay is introduced into the reference beam. The sample beam passes into a Raman cell filled with 30 atm of hydrogen gas. The resulting first Stokes beam at 683 nm is preamplified by the use of SRS with a fraction of the undelayed reference beam at 532 nm. The preamplified Stokes light passes through the turbid sample and into a third Raman cell. The reference beam is delayed to overlap the early light from the sample, resulting in amplification of only the early light. The contrast of the gate is determined by the ratio of the light transmitted when the reference pulse is off. The Stokes light is split off and detected using a CCD or a streak camera. This method does not rely on the field-coherence properties of the light and, therefore, an ultrashort laser pulse is required, the duration of which determines the length of the transmission time window.

In addition to having different spatial-angular and temporal characteristics than the diffusive light, the ballistic and/or snake photons retain much of their coherence and phase properties, as opposed to the diffusive light, which loses these properties. Several coherent, nonlinear optical techniques that take advantage of the coherent field characteristics of the early light to provide ultrafast time gating have been devised. One such field-coherence method is based on holography. Light from a femtosecond-pulsed laser is split into a sample beam and a reference beam that has an adjustable optical delay by a Mach-Zehnder interferometer. See, e.g., "Two-Dimensional Imaging Through Diffusing Media Using 150-fs Gated Electronic Holography Techniques," by H. Chen et al., Opt. Lett. 16, 487 (1991). An ultrafast source is described and used by the authors, but a slower pulse having an appropriate bandwidth could also have been employed. The sample beam was passed through the turbid medium and recombined with the reference beam using a beam splitter. The optical delay was adjusted to overlap the reference beam with the early light from the sample beam. The resulting beam was directed onto a CCD camera in which images from many pulses can be averaged. Because the early light retains most of its coherence properties, it interferes with the reference beam light. The resulting interferogram contains the desired image. One drawback of this technique is that the diffusive light also impinges on the CCD camera, adding an unwanted, uniform background and decreasing the contrast of the fringes. A Fourier spatial filter might be placed in the sample beam after the scattering medium to overcome this difficulty.

Another technique that relies on the field-coherence properties of ballistic and/or snake photons for discrimination against the diffusive light is based on coherent anti-Stokes Raman Spectroscopy (CARS), where interference between sample and reference beams controls the length of the transmission window. The early light that exits the sample is coherent and will interfere with the reference beam, producing an ultrafast gate, where the coherence time of the laser pulse controls the length of the gate and can be shorter than the pulse gate. As a result, long pulse or cw lasers can be used for illumination.

Reintjes et al., supra, have used both SRS and CARS to implement correlation gating. In the CARS experiment, 566 nm dye laser pulses 8 ns in duration were split into a pump beam with an optical delay line and a sample beam. The sample beam passed through a Raman cell that contained hydrogen to produce first Stokes radiation at 740 nm. The bandwidth of the pump light was approximately 140 cm$^{-1}$, corresponding to a coherence time of 240 fs. The measured width of the correlation peak without scattering was approximately 250 fs, in close agreement with the coherence time. The Stokes radiation was directed through a mask that consisted of 0.5 mm bars and a 6 mm thick sample of raw chicken. The transmitted Stokes light entered a CARS cell crossed with the appropriately delayed pump beam at a small angle, which ensured phase matching. Anti-Stokes radiation that contained the image at 458 nm was produced and detected using a CCD camera. Sharp images of the test bar pattern were produced at optimal delay, but the image was found to degrade quickly with changes in optical delay of more than 1 ps.

Degenerate four-wave mixing experiments in absorbing dyes have been reported. However, the phase-conjugate replica of the probe beam that is generated as a result of the nonlinear polarization produced in the medium generally decays slowly, which is indicative of a thermally induced effect. See, e.g., "Optical Phase Conjugation In Laser Dyes," by R. Vijaya et al., Opt. Quant. Electron. 24, 575 (1992). The dyes employed have low fluorescence quantum yield so that nonradiative transitions dominate, and energy from the laser ends up heating the solution locally.

Accordingly, it is an object of the present invention to provide an apparatus and method for detection of ballistic light and rejection of unwanted diffusive light in order to image structures inside highly scattering media using electronically allowed transitions in atoms and molecules in the media.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus for imaging structure in a turbid medium may include: means for generating first, pulsed electromagnetic radiation having a chosen wavelength and coherence time; means for separating the first, pulsed electromagnetic radiation into a probe beam and a pump beam; an optical cell containing a chosen material such that a portion of the first, pulsed electromagnetic radiation entering the cell is absorbed, while the remainder thereof may exit the optical cell; means for directing the pump beam into the cell; means for directing the probe beam through the turbid medium, whereby the portion of the probe beam which exits the turbid medium and which contains ballistic and snake components, which maintain information concerning the structure, and a diffusive component which has lost such information, enters the optical cell such that the probe beam and the pump beam may interfere with one another, creating thereby a grating having sinusoidal spatial variation in refractive index at the chosen wavelength of first pulsed electromagnetic radiation in the material; means for introducing an optical delay into the probe beam to compensate for path differences between the probe beam and the pump beam; means for generating a second, pulsed electromagnetic radiation having a chosen wavelength and directing the second, pulsed electromagnetic radiation into the optical cell approximately collinear to, but in the opposite direction to the pump beam, whereby the second, pulsed electromagnetic radiation is scattered by the grating formed in the chosen material in the optical cell; and means for detecting the scattered electromagnetic radiation, whereby an ultrafast time gate is generated in the chosen material in the optical cell which discriminates between the ballistic and snake components, and the diffusive component of the probe beam which exit the turbid medium.

It is preferred that the means for generating the second, pulsed electromagnetic radiation having a chosen wavelength and for directing the second, pulsed electromagnetic radiation into the optical cell approximately collinear to, but in the opposite direction to the pump beam, includes means for retroreflecting the pump beam radiation unabsorbed by the chosen material in the optical cell back into the optical cell, whereby the resulting scattered electromagnetic radiation is the phase conjugate of the probe beam.

In another aspect of the present invention, in accordance with its objects and purposes, the method for imaging structure in a turbid medium may include the steps of: generating first, pulsed electromagnetic radiation having a chosen wavelength and coherence time; separating the first, pulsed electromagnetic radiation into a probe beam and a pump beam; directing the pump beam into an optical cell containing a chosen material such that a portion of the first, pulsed electromagnetic radiation entering said cell is absorbed, while the remainder thereof may exit the optical cell; directing the probe beam through the turbid medium, whereby the portion of the probe beam which exits the turbid medium and which contains ballistic and snake components, which maintain information concerning the structure, and a diffusive component which has lost such information, enters the optical cell such that the probe beam and the pump beam may interfere with one another, creating thereby a grating having sinusoidal spatial variation in refractive index at the chosen wavelength of first pulsed electromagnetic radiation in the material; introducing an optical delay into the probe beam to compensate for path differences between the probe beam and the pump beam; generating a second, pulsed electromagnetic radiation having a chosen wavelength and directing the second, pulsed electromagnetic radiation into the cell approximately collinear to, but in the opposite direction to the pump beam, whereby the second, pulsed electromagnetic radiation is scattered by the grating formed in the chosen material in the optical cell; and detecting the scattered electromagnetic radiation, whereby an ultrafast time gate is generated in the chosen material in said cell which discriminates between the ballistic and snake components, and the diffusive component of the probe beam which exit the turbid medium.

Preferably, the step of generating a second, pulsed electromagnetic radiation having a chosen wavelength and of directing the second, pulsed electromagnetic radiation into the optical cell approximately collinear to, but in the opposite direction to the pump beam, is achieved by retroreflecting pump beam radiation unabsorbed by the chosen material in the optical cell back into the optical cell, whereby the resulting scattered electromagnetic radiation is the phase conjugate of the probe beam.

Benefits and advantages of the present invention include the possibility for the detection of ballistic and snake light in an optical mammography setting, thereby greatly improving the current state of the art.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings:

FIG. 6a illustrates the situation where no cell is placed in the probe beam with the cross hairs; FIG. 6b has a cell filled with water in the probe beam with the cross hairs; FIG. 6c is a single-shot image of the cross hairs through a suspension of whole milk in water place in the probe beam; and FIG. 6d is a 50-shot average of the cross hairs through the suspension utilized in FIG. 6c hereof.

DETAILED DESCRIPTION

Briefly, the present invention includes an apparatus and method for detection of ballistic light and rejection of unwanted diffusive light in order to image structures inside highly scattering media using degenerate four-wave mixing (DFWM) of laser light to provide an ultrafast correlation time gate to discriminate against light that has undergone multiple scattering and has, thereby, lost memory of the structures inside the scattering medium. The observed signal in DFWM arises from the interference between a probe beam, which first interrogates the sample under investigation, and a forward pump-beam in an absorbing medium. The interference generates an optical fringe pattern consisting of a sinusoidal variation in the intensity of the light which translates into a sinusoidal spatial variation in the number of excited- and ground-state molecules in the absorbing medium. These alternating regions have different refractive indices for photons at the DFWM wavelength, and form a Bragg "grating". This "grating" scatters the forward pump beam after it is permitted to exit the absorbing medium and then is returned thereto along its exit path (at this point the pump beam is called the backward pump-beam), forming thereby the DFWM signal. It can be shown that a resonant enhancement of the DFWM signal occurs whenever the applied electromagnetic frequency is resonant with an allowed molecular transition in the absorbing medium. In the situation where nonradiative processes dominate in the absorbing medium, a similar, but longer-lived "thermal" grating is generated.

Figure 1:
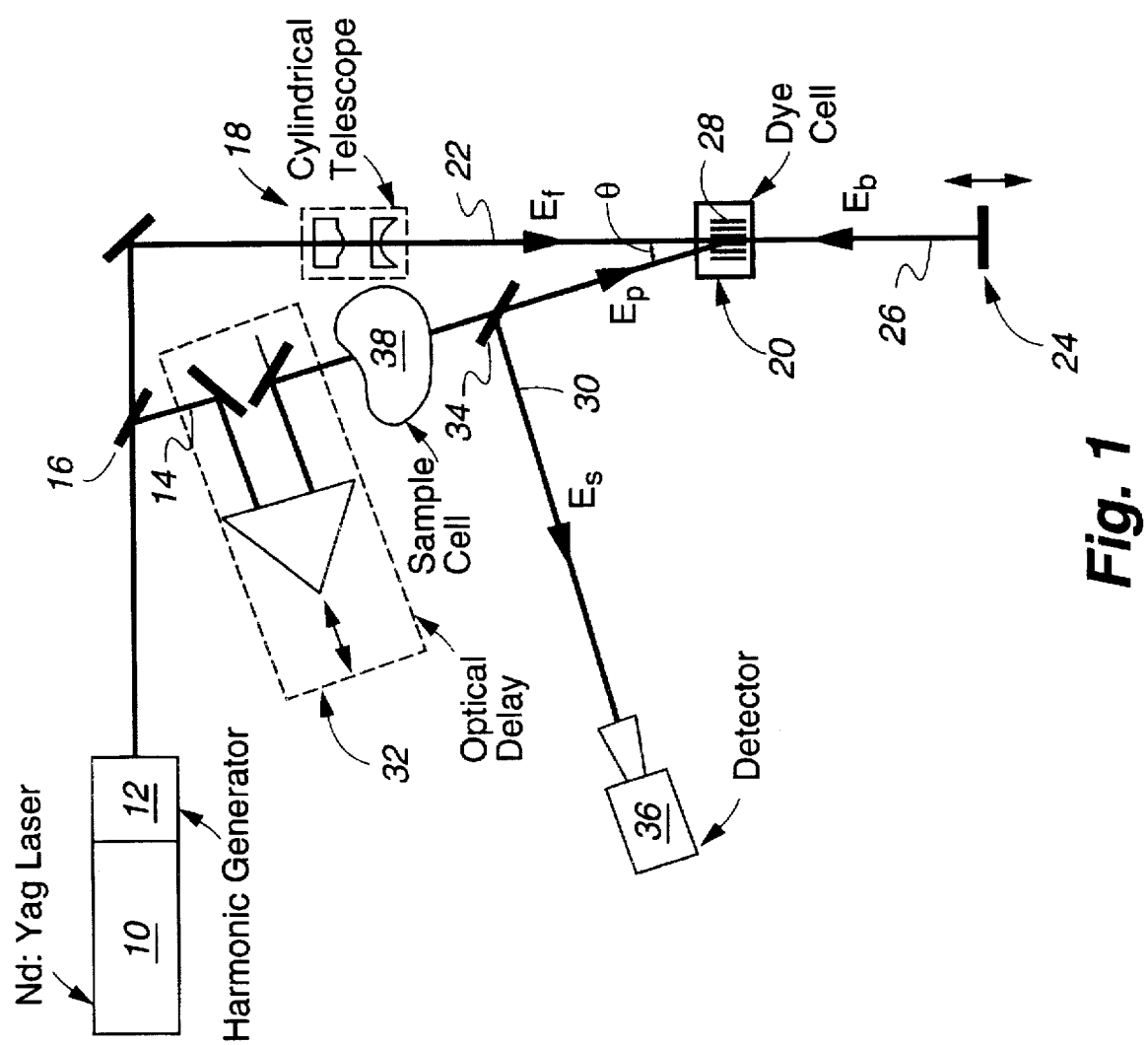
FIG. 1 is a schematic representation of the apparatus of the present invention, showing the relationship among the forward pump-beam, backward pump-beam, probe beam, and signal beam in the degenerate four-wave mixing process.

Reference will now be made in detail to the present preferred embodiments of the invention, examples of which are illustrated in the accompanying drawings. Similar or identical structure is identified with identical callouts. Turning now to FIG. 1, the apparatus of the present invention is shown. Gaussian pulses having 7 ns pulsewidth and 1.0 cm$^{-1}$-bandwidth are generated by Nd:YAG laser, 10, and doubled by second harmonic generator, 12, to produce 532 nm light having a 1.4 cm$^{-1}$ bandwidth. About 10% of the 532 nm light so produced is split from the main beam to form probe beam, 14, by beam splitter, 16. The remaining 90% is fashioned into a thin sheet by a cylindrical telescope, 18, and directed into dye cell, 20, as forward pump beam $E_f$, 22. Cell 20 is filled with rhodamine 590 (R590), typically at a concentration of 2.6×10$^{-5}$M in methanol. The intensities of the forward pump-beam 22 and probe beam 14 were about 64 and 0.45 MW/cm$^2$, respectively. The pump beam was made to traverse dye cell 20 along the front face thereof in order to minimize the amount of dye solution that the weaker probe beam must transit to reach the sheet. Light exiting the dye cell is retroreflected with a variable time delay introduced by movable mirror, 24, back through the dye cell to form backward pump-beam, $E_b$, 26, which, as stated hereinabove, is scattered by the grating, 28, generated by the interference of $E_f$ and $E_p$, forming thereby $E_s$, 30. Probe beam 14, which has a circular cross section, enters dye cell, 20, through the front face thereof and intersects the sheet formed by the forward and backward pump beams at an angle of (typically) 22°. An optical delay is introduced in the probe-beam line by mirror system, 32, to compensate for optical path differences between the forward pump-beam and the probe beam, allowing the two beams to more effectively interfere in the dye. The phase-conjugate signal beam 30 is extracted using an approximately 25% dichroic mirror, 34, to a CCD detector or a power meter, 36. As can be seen from FIG. 1, the forward and reverse pump-beams counterpropagate. Since they are also at the same wavelength, phase matching for the probe beam occurs for all crossing angles, θ, thereby eliminating the exacting geometric requirements of a CARS measurement. Phase-matching conditions require that the generated signal beam be the complex conjugate of the probe beam. This fact can be used to facilitate separation of the probe and signal beams which also are the same wavelength. In a typical DFWM imaging experiment, $E_f$ and $E_p$ have parallel polarizations that are oriented at 90° with respect to $E_b$. This causes $E_s$ and $E_p$ to have crossed polarizations, thereby allowing efficient discrimination of $E_p$ in the detection of $E_s$. It should be mentioned that polarization techniques are unnecessary in the performance of DFWM experiments, and for reasons of simplicity the polarizations of all three incident beams were parallel and vertical in the experiments described hereinbelow. The complex-conjugate nature of the signal beam causes any distortion of the probe beam by windows or by nonuniformities in the medium to be completely removed as the signal beam retraces the probe-beam path. This is not the case for similar measurements using CARS. The probe beam splitter 16 was 10% reflecting at 45° incidence for s polarized light. The signal beam splitter 34 was 30% reflecting for p-polarized light at 45° incidence. Scattering cell, 38, containing cross hairs was inserted into the probe beam, as will be described hereinbelow.

Having generally described the invention, the following example illustrates the specific details thereof.

EXAMPLE

Experiments have been performed with the apparatus described in FIG. 1 in order to determine the nature of the grating formed in the dye cell, to measure the coherence time of the laser, to prove the phase-conjugate nature of the signal beam, and to determine the dependence of the signal (reflectivity) on dye concentration and laser intensity. Finally, images of test cross-hair pattern have been obtained through highly turbid suspensions of whole milk in water that are opaque to the naked eye.

Figure 2:
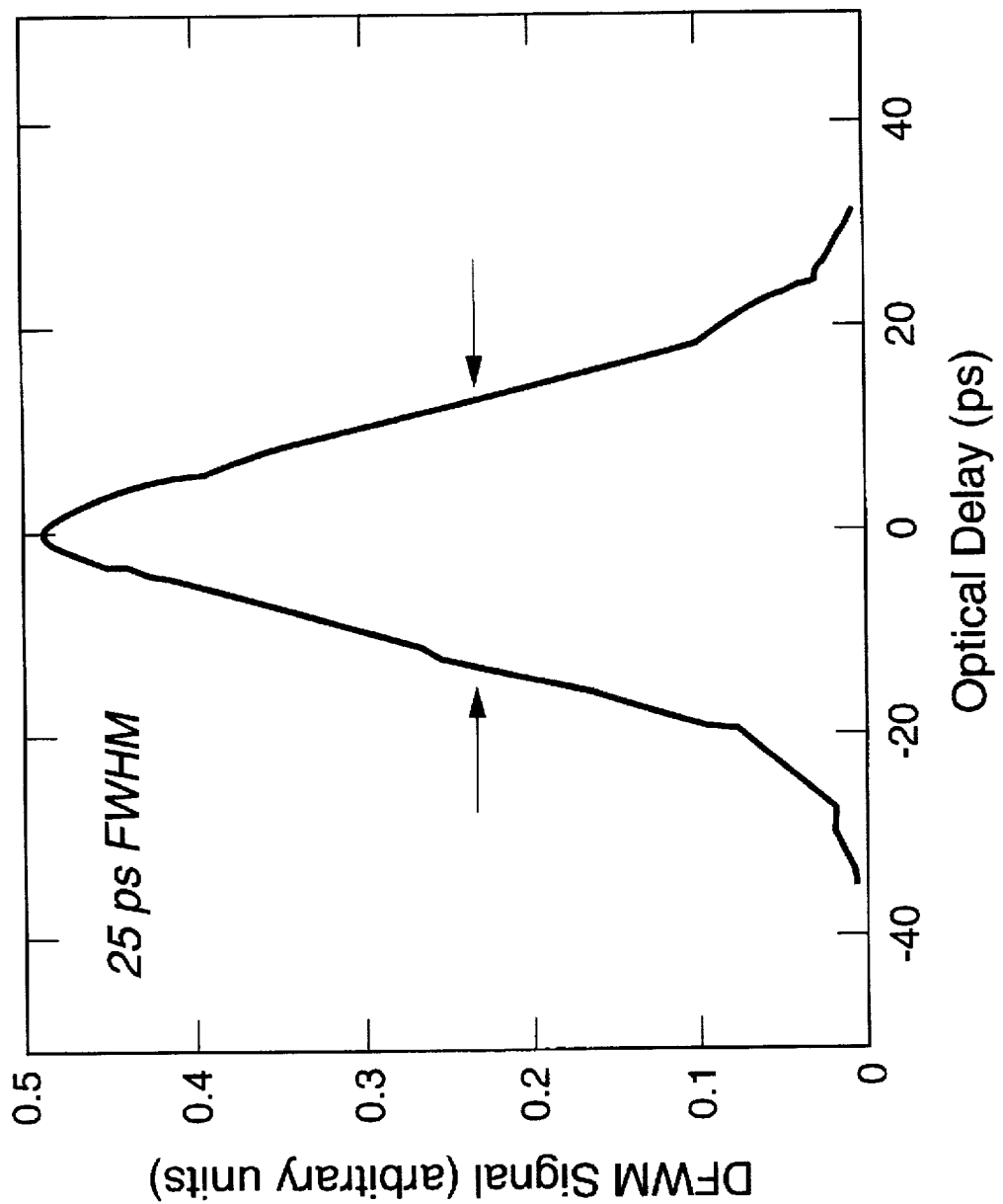
FIG. 2 shows the phase-conjugated signal generated using the apparatus illustrated in FIG. 1 hereof, as a function of delay between the forward pump-beam and the probe-beam, and demonstrates that degenerate four-wave mixing can provide an ultrafast gate.

FIG. 2 is a plot of the phase-conjugated signal intensity as a function of optical delay between the forward pump and probe beams. The delay is varied by moving mirror system 32 shown in FIG. 1, hereof. The bandwidth of the 532 nm pump laser is approximately 1.4 cm$^{-1}$, yielding a coherence time of about 24 ps. Correspondingly, the measured FWHM of the signal versus the optical delay curve shown in FIG. 2 is ~25 ps and has an approximate Gaussian shape. FIG. 2 thus demonstrates the facility of DFWM for providing an ultrafast optical gate for the ballistic photons. It is estimated that the contrast of the gate with no scattering cell present is about 250. By varying the coherence time, the gating time can be further reduced or increased to optimize imaging through extremely turbid media such as human breast tissue. A shorter coherence time (or a wider bandwidth) will increase the contrast of the gate.

Figure 3:
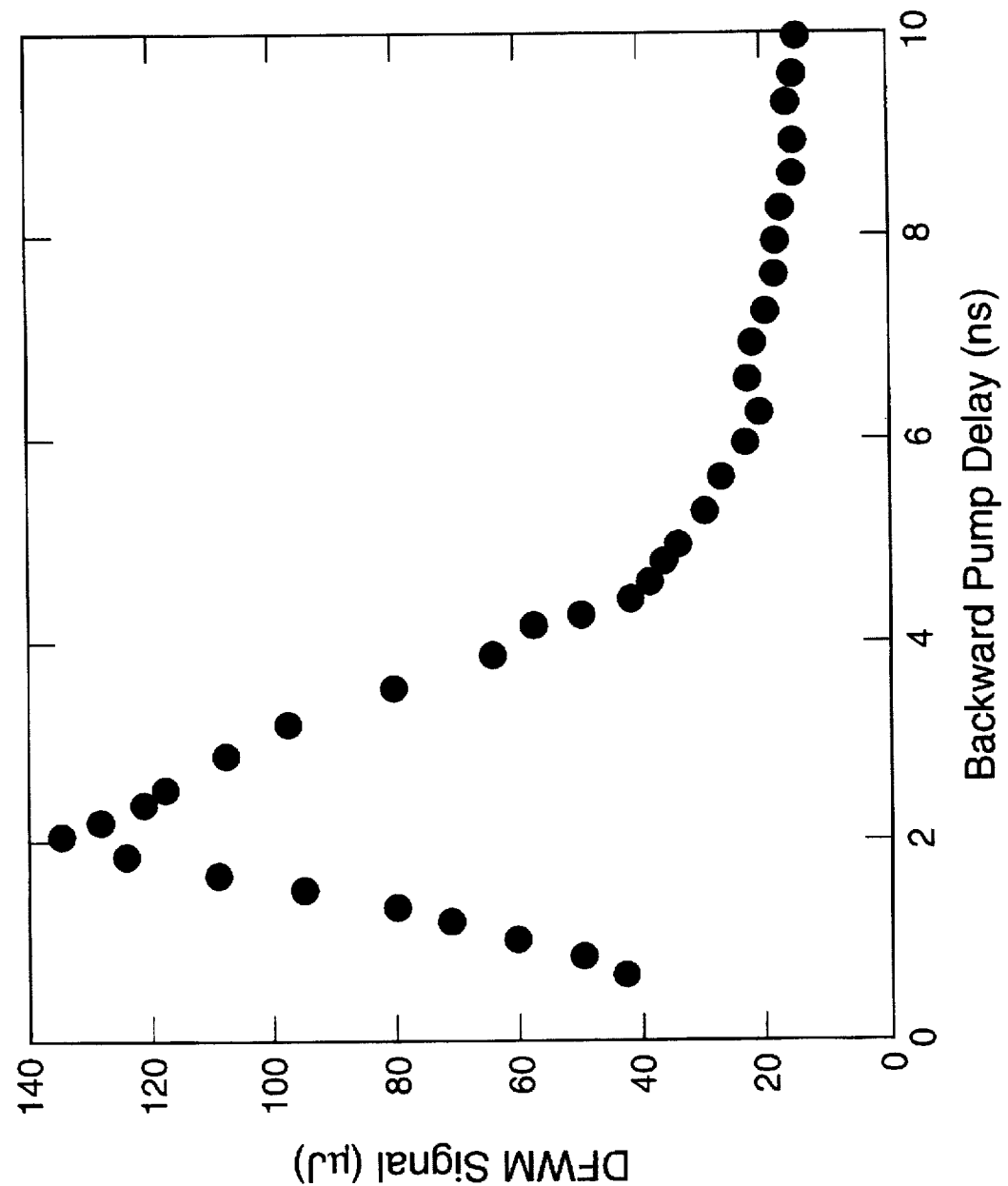
FIG. 3 shows the phase-conjugate signal generated using the apparatus illustrated in FIG. 1 hereof, versus delay between the grating formation and the signal readout, the optical delay being controlled by movement of the end mirror.

Increasing the optical delay by moving end mirror 24 shown in FIG. 1 hereof, increases the amount of time between grating formation and readout, and therefore permits the measurement of grating lifetime. This effect is illustrated in FIG. 3 hereof. Unlike previous DFWM experiments in absorbing dyes, the grating is observed to decay quickly after it is excited by the forward pump and probe beams. This indicates that the grating is not a thermal one, which would have a decay constant of several microseconds. By contrast, the data suggest an excited-state grating which decays at approximately the 5 ns lifetime of R590. The initial rise in the curve may be due to the initial rise in energy of the laser pulse, indicating that a high pump-pulse energy is required for production of such gratings. The saturation intensity for the R590 solution employed has been measured to be ~10 MW/cm$^2$. The data shown in FIG. 3 were obtained at a forward pump-beam intensity of 64 MW/cm$^2$ and a probe-beam intensity of 0.45 MW/cm$^2$, which yields an intensity at the grating substantially greater than the saturation intensity. Thus, the dominant contribution to the measured signal must be from an excited-state grating. The slowly decaying, nonzero, residual signal evident at delay times greater than about 6 ns may be the result of a thermal-grating background signal.

Figure 4:
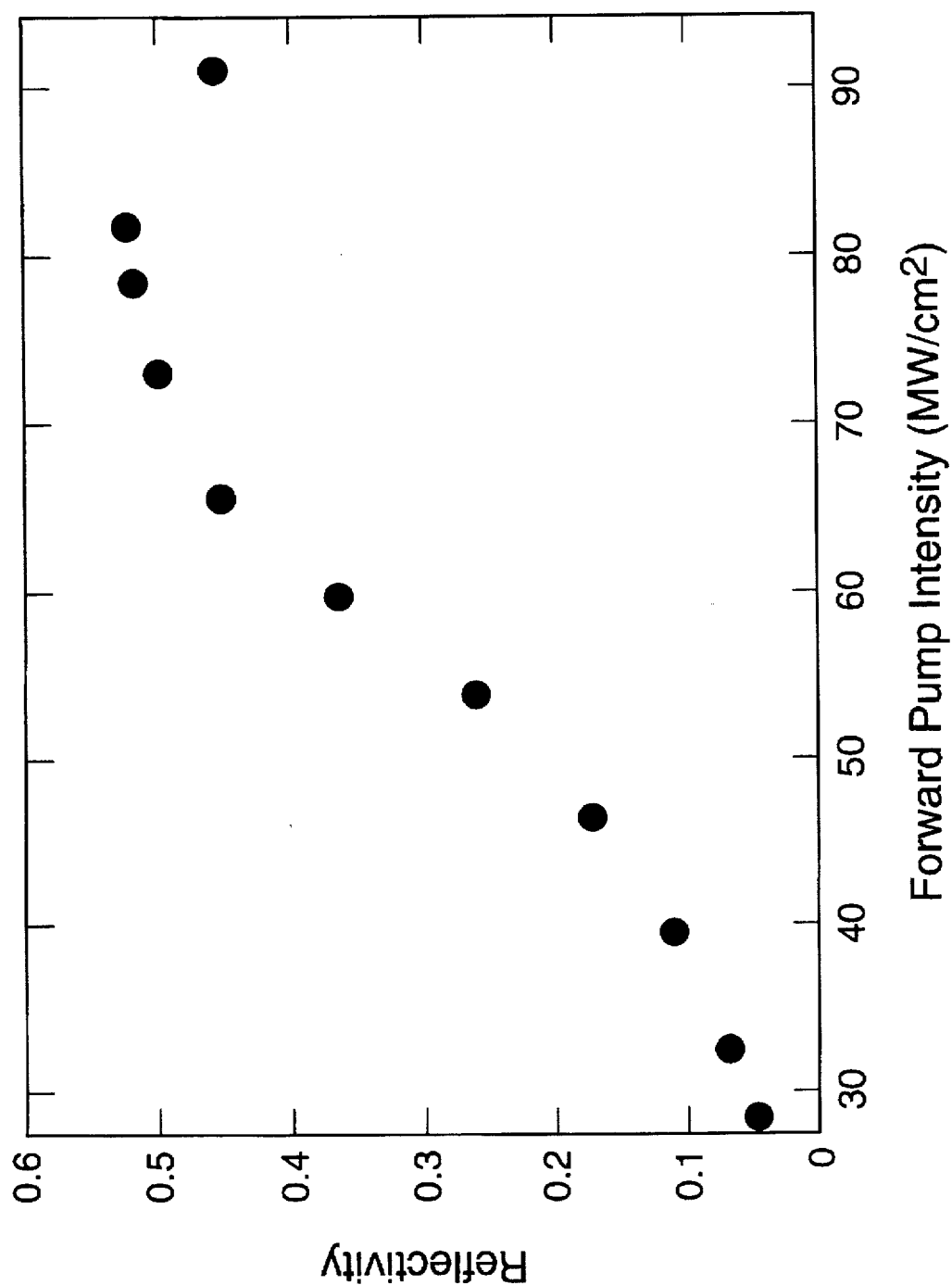
FIG. 4 shows the reflectivity of the phase-conjugate mirror generated using the apparatus illustrated in FIG. 1 hereof, as a function of the forward pump-beam intensity.

FIG. 4 is a plot of the phase-conjugate reflectivity as a function of forward pump intensity. The reflectivity exhibits a quadratic relationship with pump-beam intensity for intensities <60 MW/cm$^2$, reaching about 50% at relatively high pump intensity, and then saturating. It can be shown that both for thermal and excited-state gratings, the reflectivity depends on the product of the forward pump-beam intensity squared, for low pump intensities, while for excited-state gratings, where the intensity is greater than the saturation intensity, the reflectivity becomes proportional to the inverse of the forward pump-beam intensity; hence, reflectivity saturates and begins to decrease. The R590, employed according to the present invention, and the DCM used in the experiments by Vijaya et al., supra, have high fluorescence quantum yields, show saturation behavior, and form excited-state gratings.

Figure 5:
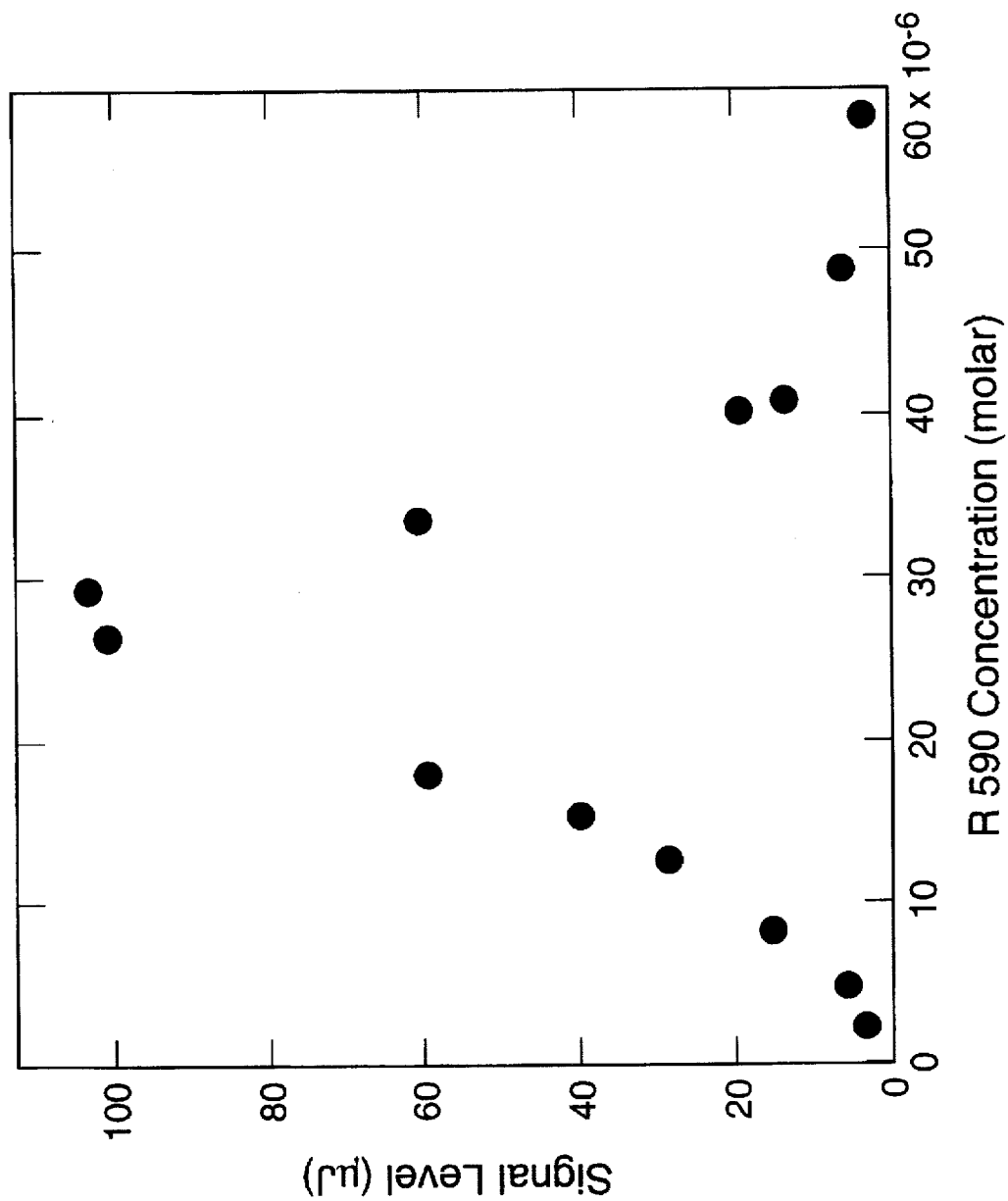
FIG. 5 shows the phase-conjugate signal generated using a slightly different geometry from the apparatus illustrated in FIG. 1 hereof, as a function of dye concentration, and clearly indicates the sharp dependence of the signal on dye concentration, the signal decay at high dye concentrations being caused by probe-beam absorption.

FIG. 5 shows the behavior of the phase-conjugate signal as a function of R590 concentration, and demonstrates the importance of dye concentration on signal level. The data were obtained for a constant forward pump-beam intensity of 64 MW/cm$^2$ and a probe-beam intensity of 0.45 MW/cm$^2$, the two beams intersecting at 12°. The signal rises approximately quadratically with dye concentration, reaches a maximum value and decays for concentrations in excess of $2.6 \times 10^{-5}$M. Reoptimization of the dye concentration was not performed for the apparatus illustrated in FIG. 1 hereof; however, because the probe-beam path through the dye is minimized in the present apparatus, the optimum dye molarity is expected to be somewhat higher than $2.6 \times 10^{-5}$M.

Figure 6:
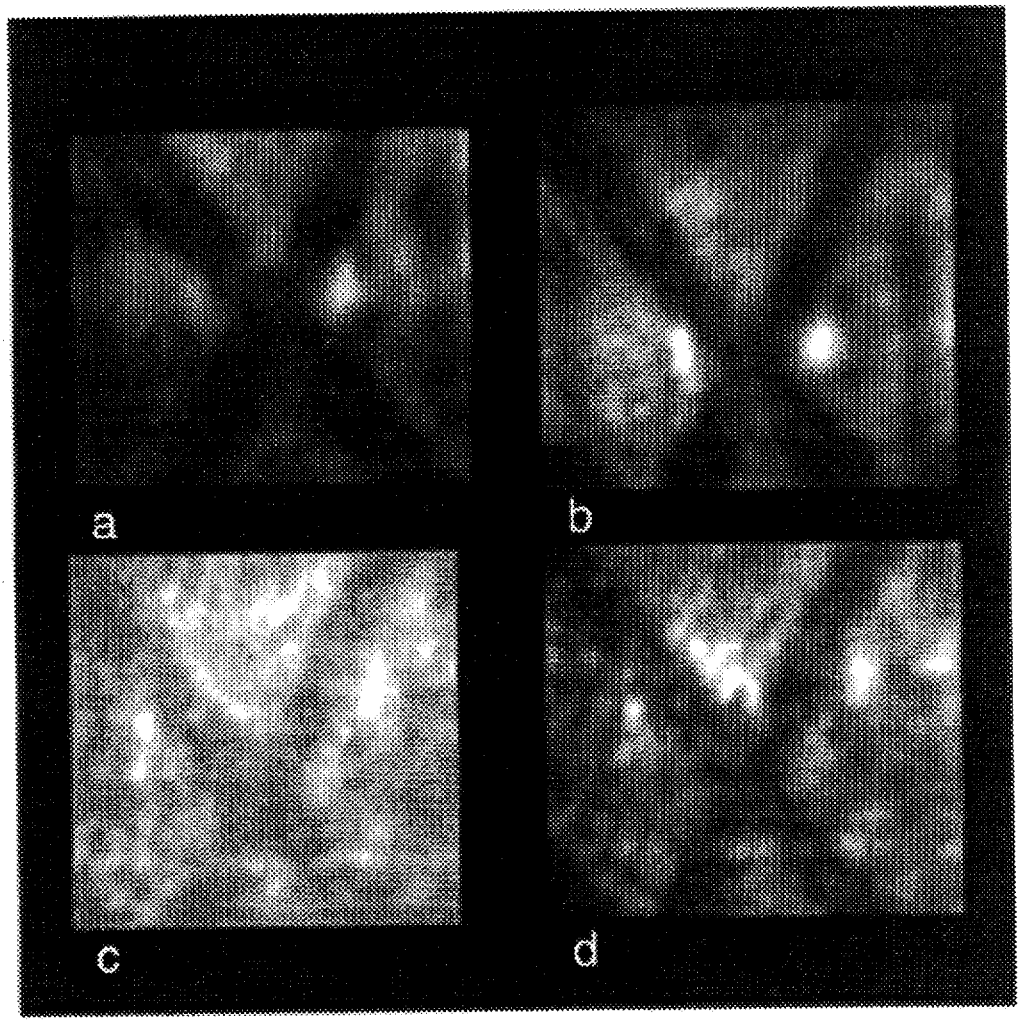
FIGS. 6a–d are four images of 200 μm cross hairs inserted into the probe beam in the apparatus illustrated in FIG. 1 hereof.

FIG. 6 shows four images of cross hairs obtained using the present invention. The cross hairs are ~200 μm thick. FIG. 6(a) shows a single shot image obtained when no scattering cell is present in the beam, providing a baseline on which to judge the quality of the other images. FIG. 6(b) is the same as FIG. 6(a) but with a 5 cm cell filled with clear water placed in the position marked in FIG. 1. The optical delay was changed to account for the change in path length as a result of the water having been introduced. FIG. 6(c) shows a single-shot image of the cross hairs through a turbid suspension of whole milk in water. The turbidity of the 5 cm path length of suspension was sufficient to completely obscure fluorescent room when viewed through the suspension. FIG. 6(d) is a 50 shot average of the cross hairs through the same suspension as in FIG. 6(c). It may be observed from these Figures that the signal-to-noise ratio is not good even in the absence of the sample cell. For example, the signal-to-noise ratio of FIG. 6(d) is about the same as that for FIG. 6(c). This is due to inhomogeneities in the laser beam, which are quite pronounced and constant from shot-to-shot, and hence cannot be averaged away. Such inhomogeneities may be eliminated by using a better laser source.

Application of DFWM for imaging through human breast tissue will require several improvements. First, wavelengths in the red or the near infrared portion of the electromagnetic spectrum will be required, since such wavelengths are transmitted relatively well by tissue. Second, higher reflectivities will be required. D. M. Bloom et al. in "Observation Of Amplified Reflection By Degenerate Four-Wave Mixing In Atomic Sodium Vapor," Opt. Lett. 2, 58 (1978), have observed a factor-of-100 amplification when the laser is operated slightly off resonance of the D lines of sodium vapor. Operating the laser off resonance minimizes beam absorption, which limits resonance reflectivities and resonantly enhances the Kerr nonlinearity, forming a third type of grating where the refractive index is altered by the region of anomalous dispersion surrounding electronic transitions rather than being altered by thermal or excited-state refractive-index effects. Since potassium vapor has its D lines in the red part of the spectrum at 766 and 770 nm, and because its outer shell electronic structure is identical to sodium vapor, potassium would be a good choice for such a reflecting amplifier.

The foregoing description of the invention has been presented for purposes of illustration and description and is not intended to be exhaustive or to limit the invention to the precise form disclosed, and obviously many modifications and variations are possible in light of the above teaching. For example, after studying the present disclosure, one having ordinary skill in the art would understand that a second, pulsed light source might be employed to supply the backward pump-beam to the optical cell, so long as the wavelength and coherence time of the generated light were chosen such that the light could effectively interact with the grating. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for imaging structure in a turbid medium, which comprises in combination:
   a. means for generating first, pulsed electromagnetic radiation having a chosen wavelength and coherence time;
   b. means for separating the first, pulsed electromagnetic radiation into a probe beam and a pump beam;
   c. an optical cell containing a chosen material such that a portion of the first, pulsed electromagnetic radiation entering said optical cell is absorbed, while the remainder thereof may exit said optical cell;
   d. means for directing the pump beam into said optical cell;
   e. means for directing the probe beam through the turbid medium, whereby the portion of the probe beam which exits the turbid medium and which contains ballistic and snake components, which maintain information concerning the structure, and a diffusive component which has lost such information, enters said optical cell such that the probe beam and the pump beam may interfere with one another, creating thereby a grating having sinusoidal spatial variation in refractive index at the chosen wavelength of first pulsed electromagnetic radiation in the material;
   f. means for introducing an optical delay into the probe beam to compensate for path differences between the probe beam and the pump beam;
   g. means for generating a second, pulsed electromagnetic radiation having a chosen wavelength and directing the second, pulsed electromagnetic radiation into said optical cell approximately collinear to, but in the opposite direction to the pump beam, whereby the second, pulsed electromagnetic radiation is scattered by the grating formed in the chosen material in said optical cell; and
   h. means for detecting the scattered electromagnetic radiation, whereby an ultrafast time gate is generated in the chosen material in said cell which discriminates between the ballistic and snake components, and the diffusive component of the probe beam which exit the turbid medium.

2. The apparatus for imaging structure in a turbid medium as described in claim 1, wherein said means for generating a second, pulsed electromagnetic radiation having a chosen wavelength and for directing the second, pulsed electromagnetic radiation into said optical cell approximately collinear to, but in the opposite direction to the pump beam, includes means for retroreflecting pump beam radiation unabsorbed by the chosen material in said optical cell back into said optical cell, whereby the resulting scattered electromagnetic radiation is the phase conjugate of the probe beam.

3. The apparatus for imaging structure in a turbid medium as described in claim 2, wherein a chosen delay is introduced in the retroreflected unabsorbed electromagnetic radiation by said retroreflecting means such that the delay between the grating formation and the scattering of the retroreflected unabsorbed electromagnetic radiation is optimized.

4. The apparatus for imaging structure in a turbid medium as described in claim 1, wherein said first, pulsed electromagnetic radiation generating means includes a frequency-doubled Nd:YAG laser, and the chosen material includes a solution of rhodamine 590.

5. The apparatus for imaging structure in a turbid medium as described in claim 1, wherein means are provided for forming the pump beam into a thin sheet which traverses said optical cell substantially along the front surface thereof in order that the probe beam traverse the minimum amount of chosen material before interacting with the pump beam.

6. The apparatus for imaging structure in a turbid medium as described in claim 1, the chosen wavelength of the first, pulsed electromagnetic radiation is selected such that the chosen wavelength is off resonance with the chosen material contained in said optical cell, so that absorption of the pump beam and probe beam in said optical cell are minimized.

7. A method for imaging structure in a turbid medium, which comprises the steps of:
   a. generating first, pulsed electromagnetic radiation having a chosen wavelength and coherence time;
   b. separating the first, pulsed electromagnetic radiation into a probe beam and a pump beam;
   c. directing the pump beam into an optical cell containing a chosen material such that a portion of the first, pulsed electromagnetic radiation entering the optical cell is absorbed, while the remainder thereof may exit the optical cell;
   e. directing the probe beam through the turbid medium, whereby the portion of the probe beam which exits the turbid medium and which contains ballistic and snake components, which maintain information concerning the structure, and a diffusive component which has lost such information, enters the optical cell such that the probe beam and the pump beam may interfere with one another, creating thereby a grating having sinusoidal spatial variation in refractive index at the chosen wavelength of first pulsed electromagnetic radiation in the material;
   f. introducing an optical delay into the probe beam to compensate for path differences between the probe beam and the pump beam;

g. generating a second, pulsed electromagnetic radiation having a chosen wavelength and directing the second, pulsed electromagnetic radiation into the cell approximately collinear to, but in the opposite direction to the pump beam, whereby the second, pulsed electromagnetic radiation is scattered by the grating formed in the chosen material in the optical cell; and h. detecting the scattered electromagnetic radiation, whereby an ultrafast time gate is generated in the chosen material in said optical cell which discriminates between the ballistic and snake components, and the diffusive component of the probe beam which exit the turbid medium.

8. The method for imaging structure in a turbid medium as described in claim 7, wherein said step of generating a second, pulsed electromagnetic radiation having a chosen wavelength and directing the second, pulsed electromagnetic radiation into the optical cell approximately collinear to, but in the opposite direction to the pump beam, is achieved by retroreflecting pump beam radiation unabsorbed by the chosen material in the optical cell back into the optical cell, whereby the resulting scattered electromagnetic radiation is the phase conjugate of the probe beam.

9. The method for imaging structure in a turbid medium as described in claim 8, further comprising the step of introducing a chosen delay in the retroreflected unabsorbed electromagnetic radiation such that the delay between the grating formation and the scattering of the retroreflected unabsorbed electromagnetic radiation is optimized.

10. The method for imaging structure in a turbid medium as described in claim 7, wherein the first, pulsed electromagnetic includes frequency-doubled Nd:YAG laser radiation, and the chosen material includes a solution of rhodamine 590.

11. The method for imaging structure in a turbid medium as described in claim 7, further comprising the step of forming the pump beam into a thin sheet which traverses the optical cell substantially along the front surface thereof in order that the probe beam traverse the minimum amount of chosen material before interacting with the pump beam.

12. The method for imaging structure in a turbid medium as described in claim 7, wherein the chosen wavelength of the first, pulsed electromagnetic radiation is selected such that the chosen wavelength is off resonance with the chosen material contained in the optical cell, so that absorption of the pump beam and probe beam in the optical cell are minimized.

* * * * *